United States Patent [19]
Lonczak et al.

[11] Patent Number: 5,944,522
[45] Date of Patent: Aug. 31, 1999

[54] AUTOMATIC CLEANING DEVICE

[75] Inventors: John Lonczak, Newburgh; Christopher Goggin, Calverton, both of N.Y.; Lester Heiman, Somerset, N.J.

[73] Assignee: Sultan Chemists, Inc., Englewood, N.J.

[21] Appl. No.: 08/845,686

[22] Filed: Apr. 25, 1997

[51] Int. Cl.[6] ............................... A61C 17/06; A61L 2/16
[52] U.S. Cl. ................... 433/91; 604/83; 433/95
[58] Field of Search ................... 433/91, 92, 95, 433/96; 604/83, 247, 902, 905

[56] References Cited

U.S. PATENT DOCUMENTS

| | | | |
|---|---|---|---|
| 3,226,733 | 1/1966 | Ashton | 4/263 |
| 3,324,855 | 6/1967 | Heimlich . | |
| 3,499,393 | 3/1970 | Bent | 103/263 |
| 3,566,869 | 3/1971 | Crowson . | |
| 3,645,497 | 2/1972 | Niboer | 433/95 |
| 3,646,678 | 3/1972 | McAlister . | |
| 3,807,401 | 4/1974 | Riggle et al. | 433/91 |
| 4,054,998 | 10/1977 | Hesselgren | 433/91 |
| 4,545,956 | 10/1985 | Gisewski et al. | 422/28 |
| 4,787,599 | 11/1988 | Nyboer | 604/902 |
| 4,921,476 | 5/1990 | Wuchimich | 604/22 |
| 5,044,953 | 9/1991 | Sullivan | 433/92 |
| 5,141,501 | 8/1992 | Atkinson et al. | 604/259 |
| 5,145,367 | 9/1992 | Kaston | 433/84 |
| 5,188,530 | 2/1993 | Trawoger et al. | 433/92 |
| 5,230,625 | 7/1993 | Sutter et al. | 433/95 |
| 5,463,792 | 11/1995 | Hogan et al. | 15/322 |
| 5,472,666 | 12/1995 | Slaby | 422/28 |
| 5,480,124 | 1/1996 | Bartlett et al. | 251/309 |
| 5,743,735 | 4/1998 | Vollstedt | 433/91 |

FOREIGN PATENT DOCUMENTS

| | | |
|---|---|---|
| 0313527 | 4/1989 | European Pat. Off. . |
| 0633751 | 1/1995 | European Pat. Off. . |
| 2853635 | 6/1980 | Germany ............. 604/905 |
| 3805609 | 9/1989 | Germany . |
| 4102182 | 2/1996 | Germany . |
| 2280607 | 2/1995 | United Kingdom . |
| 9319697 | 10/1993 | WIPO . |

*Primary Examiner*—Ralph A. Lewis
*Attorney, Agent, or Firm*—Steinberg & Raskin, P.C.

[57] ABSTRACT

An automatic cleaning device for delivering a cleaning fluid to a vacuum hose of a dental suction system is provided which automatically dispenses a measured amount of cleaning fluid into the vacuum hose each time that a dental instrument is changed. The automatic cleaning device includes a housing having a first end and a second end. The first end of the housing is adapted to releasably receive a hollow dental instrument, such as a suction tube. The second end of the housing is coupled to the vacuum hose. The housing of the automatic cleaning device includes a cavity which extends from the first end to the second end and a reservoir is disposed within the housing, the reservoir containing a cleansing fluid. A hollow piston is disposed within the housing and coupled to the first end of the housing such that receipt of the hollow dental instrument in the first end of the housing causes a forward-backward longitudinal movement of the hollow piston. The hollow piston provides an air-flow passage between the first end and the second end of the housing to provide air flow from the hollow dental instrument to the vacuum hose. A pair of longitudinally spaced apart protrusions extend outwardly from an outer surface of the hollow piston. A tab extends across a portion of the reservoir and contacts each of the protrusions during the forward-backward movement of the hollow piston. In accordance with a further aspect of this embodiment, the pair of protrusions are a pair of O-rings and the reservoir has an outer wall defined by the inner wall of the housing and has an inner wall defined by the outer surface of the hollow piston.

24 Claims, 10 Drawing Sheets

AUTOMATIC CLEANING DEVICE

FIELD OF THE INVENTION

The present invention relates to the field of devices for cleaning vacuum hoses of dental instruments.

BACKGROUND OF THE INVENTION

During the course of dental treatment, liquids containing saliva, blood, and other debris are frequently removed from the mouth of the patient by a vacuum system. The vacuum system is generally located near the treatment chair, and includes a suction tube for insertion into the patient's mouth and a vacuum hose coupled between a waste disposal unit and the suction tube. The suction tube is generally replaced before each treatment and is therefore removable from the vacuum hose.

In order to maintain acceptable hygiene, and to ensure that the vacuum hose does not become clogged, it is important to frequently clean the vacuum hose with a cleaning fluid. Traditionally, the vacuum hose was cleaned once a day by sucking a cleaning fluid through the system.

In addition, DE 43 20 095.8 purports to disclose a connector for connecting a suction tube to a vacuum hose. The connector includes a reservoir for holding a cleaning fluid, and, upon insertion of the suction tube into the connector, a defined amount of the cleaning fluid is introduced into the vacuum hose.

SUMMARY OF THE INVENTION

While Clinical Research Associates of Provo Utah, an independent research group, recommends that the vacuum hose of a dental vacuum system be cleaned daily, users of the vacuum system often forget to inject the cleaning fluid into the system after each treatment. As a result, additional waste deposits build up in the vacuum hose. Since the deposits are more difficult to remove once they have built up over time, the failure to clean the vacuum system after each treatment reduces the effectiveness of the cleaning fluid when it eventually is used. Moreover, the build up of waste deposits detrimentally affects hygiene during treatment.

In accordance with the present invention, an automatic cleaning device for delivering a cleaning fluid to a vacuum hose of a dental suction system is provided which automatically dispenses a measured amount of cleaning fluid into the vacuum hose each time that a dental instrument is changed. The automatic cleaning device includes a housing having a first end and a second end. The first end of the housing is adapted to releasably receive a hollow dental instrument, such as a suction tube. The second end of the housing is coupled to the vacuum hose. Preferably, the hollow dental instrument is secured within the first end of the housing via a friction fit so that it can be quickly and easily installed and removed, and the vacuum hose is secured to the second end of the housing by a friction fit, or clamp or the like.

The housing of the automatic cleaning device includes a cavity which extends from the first end to the second end and a reservoir containing a cleaning fluid is disposed within the housing. A hollow piston is disposed within the housing and coupled to the first end of the housing such that receipt of the hollow dental instrument in the first end of the housing causes a forward-backward longitudinal movement of the hollow piston. The hollow piston provides an air-flow passage between the first end and the second end of the housing. This passage allows air to flow from the hollow dental instrument to the vacuum hose. A pair of longitudinally spaced apart protrusions extend outwardly from an outer surface of the hollow piston. A tab extends across a portion of the reservoir and contacts each of the protrusions during the forward-backward movement of the hollow piston. As the tab contacts one and then the other of pair of the protrusions during the forward movement of the piston, cleaning fluid flows from the reservoir into the vacuum hose via the second end of the housing.

In accordance with a further aspect of this embodiment, the pair of protrusions are a pair of O-rings and the reservoir has an outer wall defined by the inner wall of the housing and has an inner wall defined by the outer surface of the hollow piston. The tab is an annular shaped member which extends outwardly from the inner wall of the housing. In accordance with another aspect of this embodiment, the hollow piston is supported within the housing by a spring which compresses as the hollow dental instrument is inserted into the first end of the housing, causing the forward movement of the piston, and then decompresses once the hollow dental instrument is secured within the first end of the housing causing the backward movement of the piston.

With this construction, a cleaning device is provided which automatically dispenses cleaning fluid into the vacuum hose each time that the hollow dental instrument is changed. Since dental instruments are routinely changed with each treatment in order to maintain proper hygiene, the cleaning device causes the cleaning fluid to be injected into the vacuum hose after each treatment. As explained above, this increases the effectiveness of the cleaning fluid and provides superior hygiene in the treatment room. Moreover, since the initial insertion of the dental instrument automatically causes a forward-backward motion of the piston, the cleaning process is completely transparent to the operator.

In accordance with a second embodiment of the present invention, the distance between the pair of protrusions is less than or equal to a longitudinal length of the tab. With this construction, a precise dosage of cleaning fluid is isolated in a chamber which is temporarily formed between the tab, the protrusions, and the outer surface of the piston as the piston travels from its initial position to its forward position.

In accordance with a further embodiment of the present invention, the automatic cleaning device includes a valve for discontinuing the flow of air from the hollow dental instrument to the vacuum hose. In accordance with a further aspect of this embodiment, the valve is a flexible elongated member such as a reed valve.

DETAILED DESCRIPTION OF THE INVENTION

Figure 1:
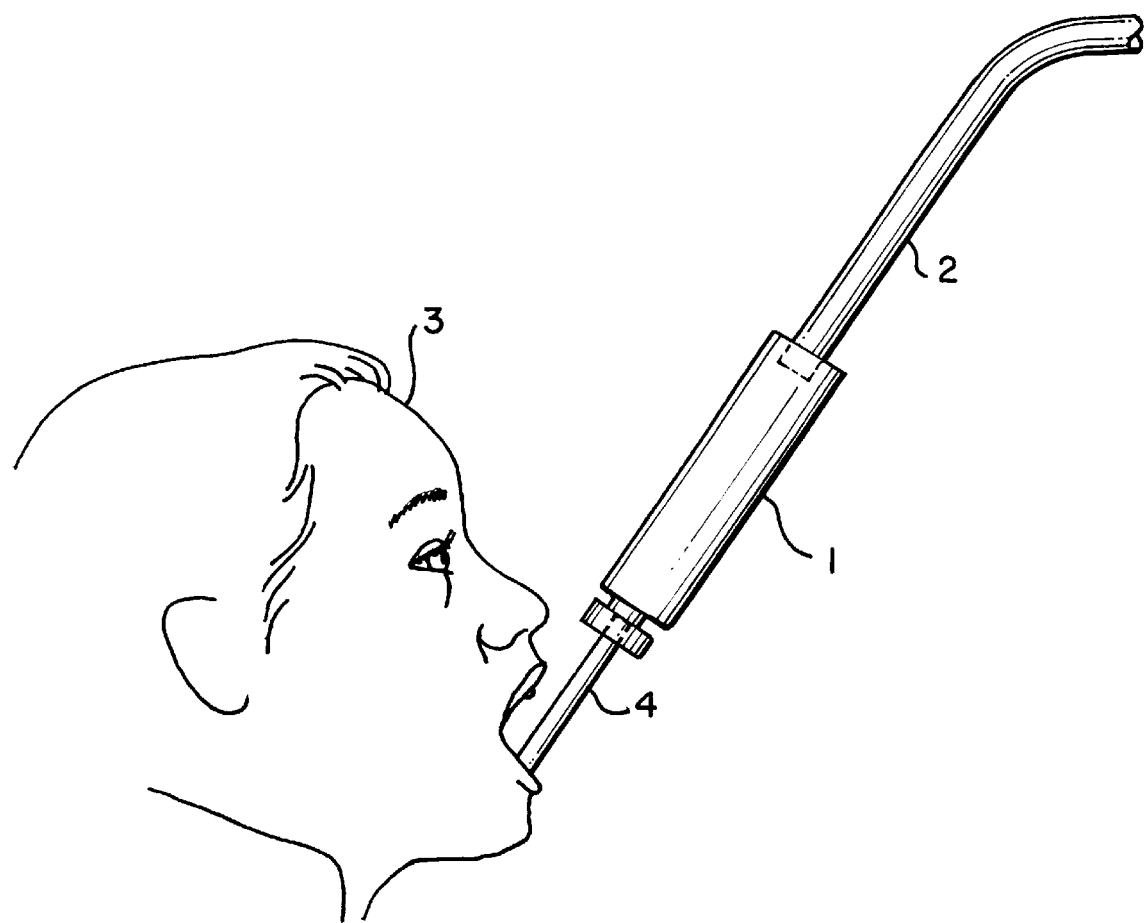
FIG. 1 shows an automatic cleaning device according to the present invention coupled between a vacuum hose and a suction tube.

FIG. 1 shows an automatic cleaning device 1 according to the present invention coupled between a suction tube 4 and a vacuum hose 2. The suction tube 4 is shown inserted into the mouth of a dental patient 3. The vacuum hose 2 is coupled to a vacuum source (not shown). During operation, saliva, blood, pus, solids and other debris from the mouth of the dental patient are sucked out of the patients mouth, through the suction tube 4, the automatic cleaning device 1, and the vacuum hose 2, and into a waste storage unit (not shown). The vacuum hose 2, suction tube 4, waste storage unit and vacuum source may be of any known construction.

In order to maintain proper hygiene, and to ensure that the vacuum hose 2 does not become clogged, it is important to frequently clean the vacuum hose with a cleaning fluid. While manufactures of cleaning fluid generally recommend that the vacuum hose of a dental vacuum system be cleaned after each treatment, users of the vacuum system often forget to inject the cleaning fluid into the system after each treatment. As a result, there is a need for a cleaning device which automatically and transparently injects cleaning fluid into the vacuum hose.

In accordance with the present invention, an automatic cleaning device is provided which provides a measured amount of cleaning fluid into the vacuum hose 2 each time that a dental instrument (illustrated as a suction tube 4 in FIG. 1) is coupled to the cleaning device. Since dental instruments are routinely changed with each treatment to maintain proper hygiene, the cleaning device causes the cleaning fluid to be injected into the vacuum hose after each treatment. As explained above, this increases the effectiveness of the cleaning fluid and provides greater hygiene in the treatment room. In accordance with the present invention, the initial insertion of the dental instrument automatically causes a forward-backward motion of the piston so that the cleansing process is completely transparent to the operator.

Figure 2:
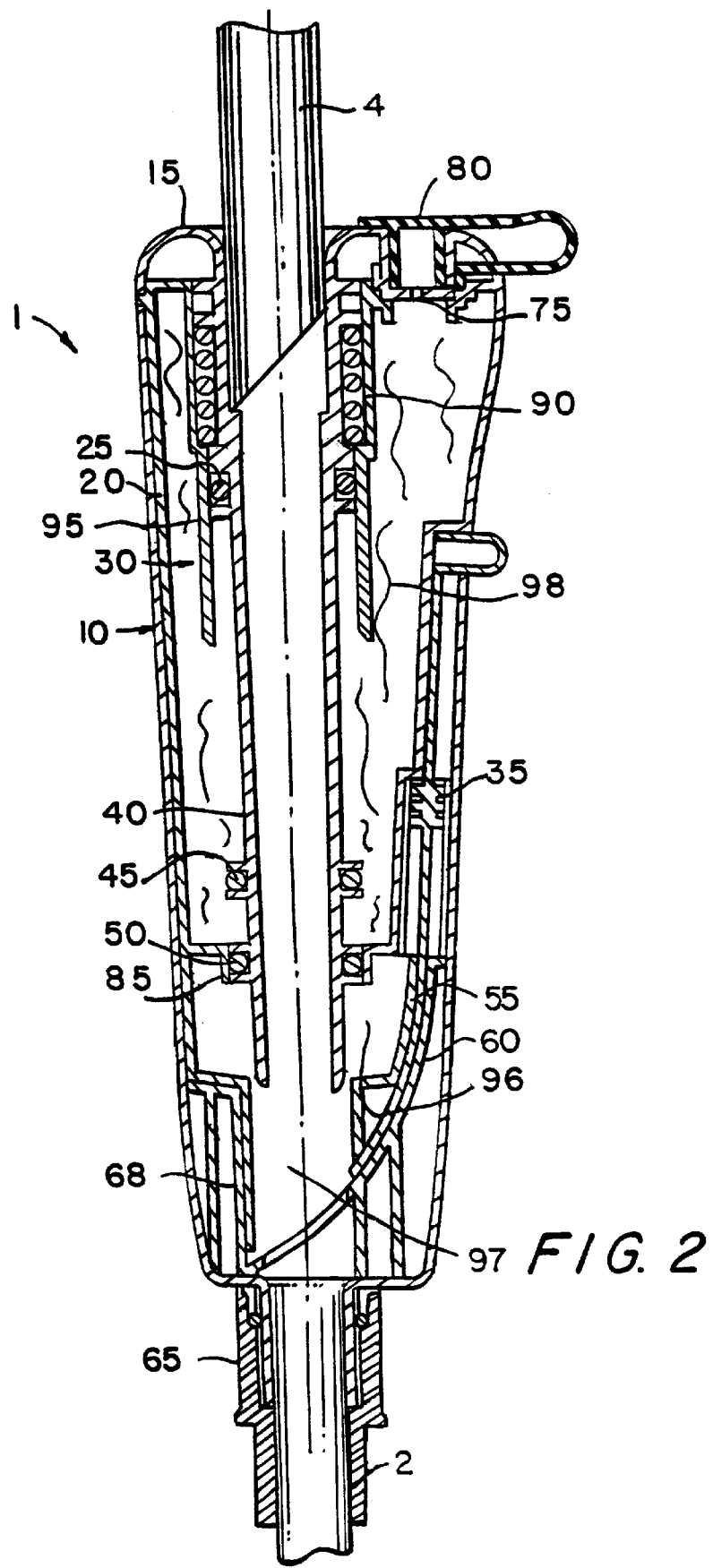
FIG. 2 shows an automatic cleaning device according to a first embodiment of the present invention.

FIGS. 2 shows a cross-section through the automatic cleaning device according to an embodiment of the present invention in more detail. The automatic cleaning device 1 includes an outer housing 10, a reservoir housing 20, a forward chamber 96, an exit chamber 97, and a hollow piston 40. A reservoir 30 is formed between the reservoir housing 20 and the piston 40. An auto-seal valve 75 and rubber seal cap 80 are mounted within the reservoir housing 20 to allow the reservoir 30 to be safely filled with cleaning fluid. The hollow piston 40 is adapted to receive the suction tube 4, the suction tube 4 being secured therein by a friction fit. Moreover, the piston 40 is mounted within springs 90 so that when the suction tube 4 is inserted into the piston 40, the piston 40 moves forward into its forward position, and then retracts to its initial position. A pair of O-rings 45, 50 are mounted around the piston 40 and an annular shaped tab 85 is formed on the interior of the reservoir housing 20. The tab 85 engages O-ring 50 in its initial position and O-ring 45 in its forward position. O-ring 25, which remains in contact with tab 95 during piston 40's full range of movements, operates as a seal to prevent the cleaning fluid from leaking out of the automatic cleaning device. A reed valve 35 is provided to allow the suction to the patient's mouth to be turned off without turning off the vacuum source. The reed valve 35 is slidably mounted within a reed valve guide 55, 60. The reed valve guide 55, 60 allows the reed valve 35 to slide across the exit chamber 97 to block the flow of air from the automatic cleaning device 1 to the vacuum hose 2.

When the piston 40 is in its initial position (as shown in FIG. 2), O-ring 50 is in contact with tab 85, and O-ring 45 is disengaged from tab 85. As the piston 40 moves forward, O-ring 50 disengages from tab 85 and cleaning fluid 98 flows from the reservoir 30 into forward chamber 96. As the piston 40 reaches its forward position, O-ring 45 is engaged with tab 85, and flow of cleaning fluid flows-into the forward chamber 96 stops. Naturally, the exact amount of cleaning fluid will be somewhat dependent upon the amount of time it takes the piston to move from its initial position to its forward position. Then, as the piston 40 returns to its initial position, the cleaning fluid in the forward chamber 96 is released into the vacuum hose 2. It should be noted that an additional amount of cleaning fluid may be sucked from the reservoir into the forward chamber 96 (and into the vacuum hose) as the piston returns to the initial position from the forward position.

In accordance with a second embodiment of the present invention, tab 85 has a length which is at least equal to the distance between O-ring 45 and O-ring 50 so that a precise dosage of cleaning fluid is applied to the vacuum hose each time the suction tube is changed. This construction is shown in FIGS. 3 through 6. The components of FIGS. 3 through 6 are identical to the components of FIG. 2, except for the length of tab 85. Therefore, certain details shown in FIG. 2 have been omitted from FIGS. 3 through 6 for ease of illustration.

Figure 3:
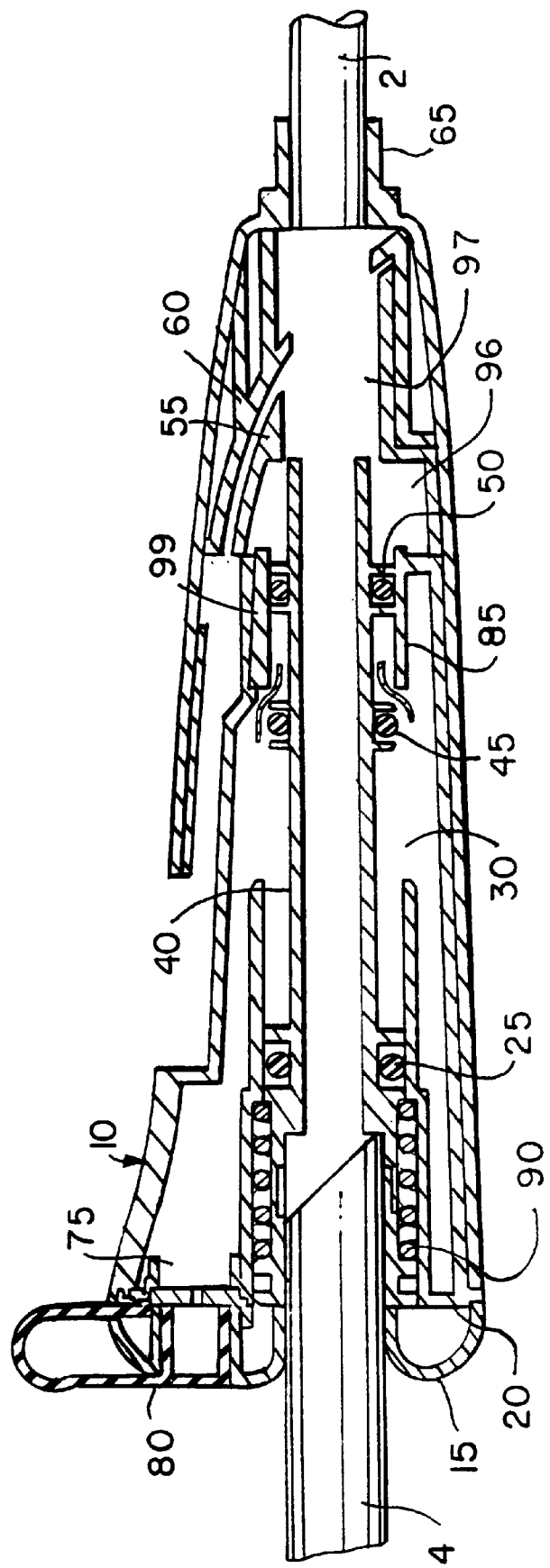
FIG. 3 shows the automatic cleaning device according to a second embodiment of the present invention in a first position.
Figure 4:
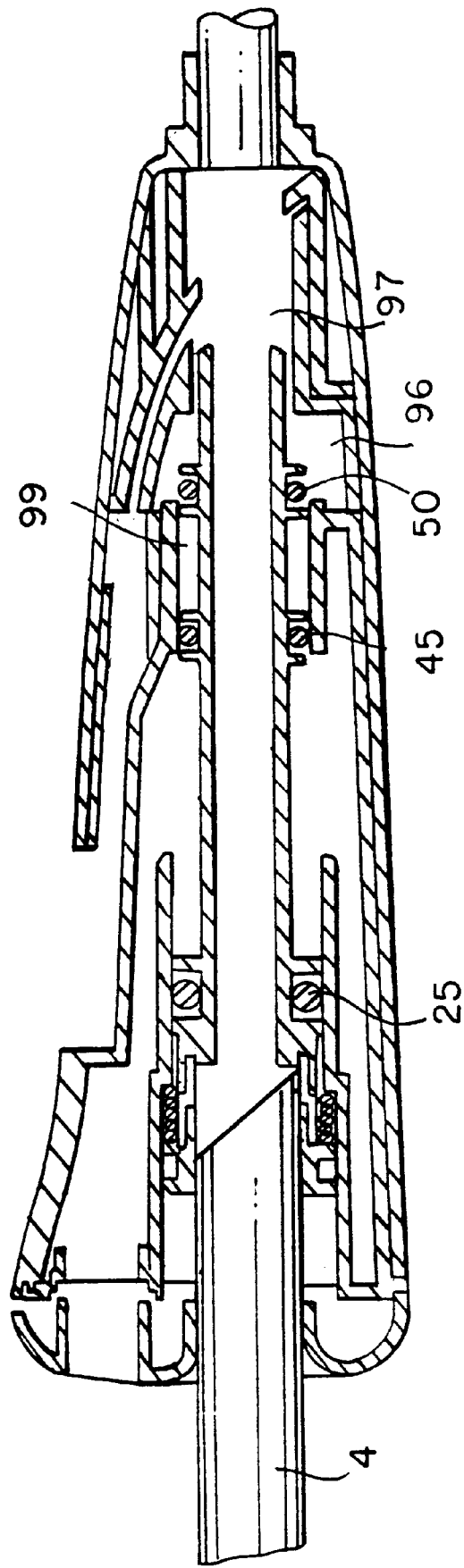
FIG. 4 shows the automatic cleaning device of FIG. 3 in a second position.
Figure 5:
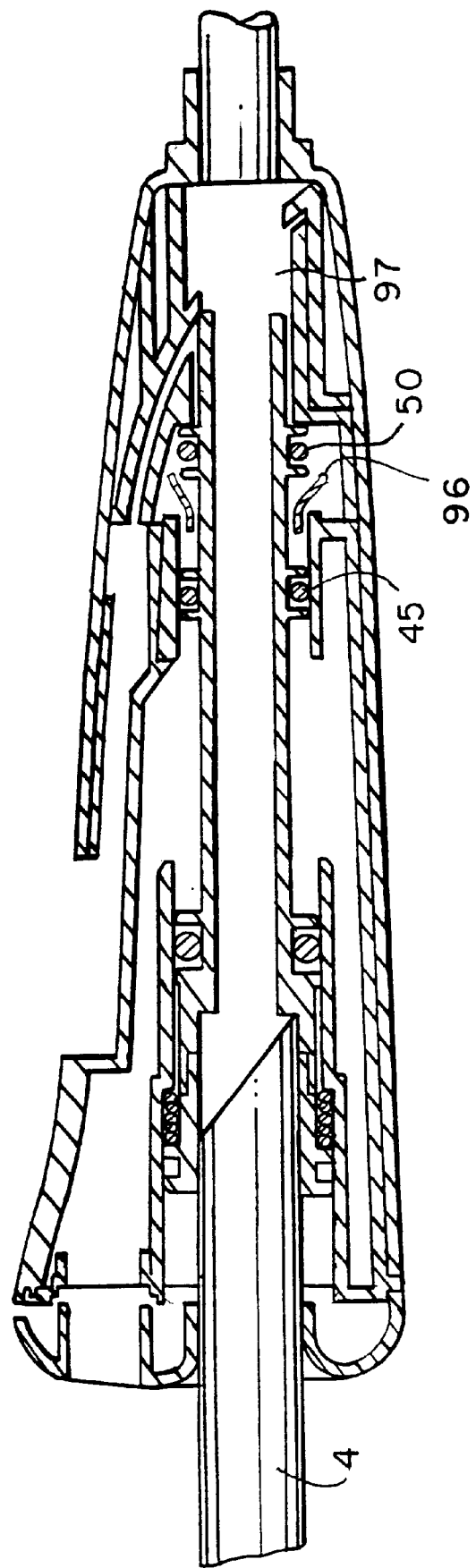
FIG. 5 shows the automatic cleaning device of FIG. 3 in a third position.
Figure 6:
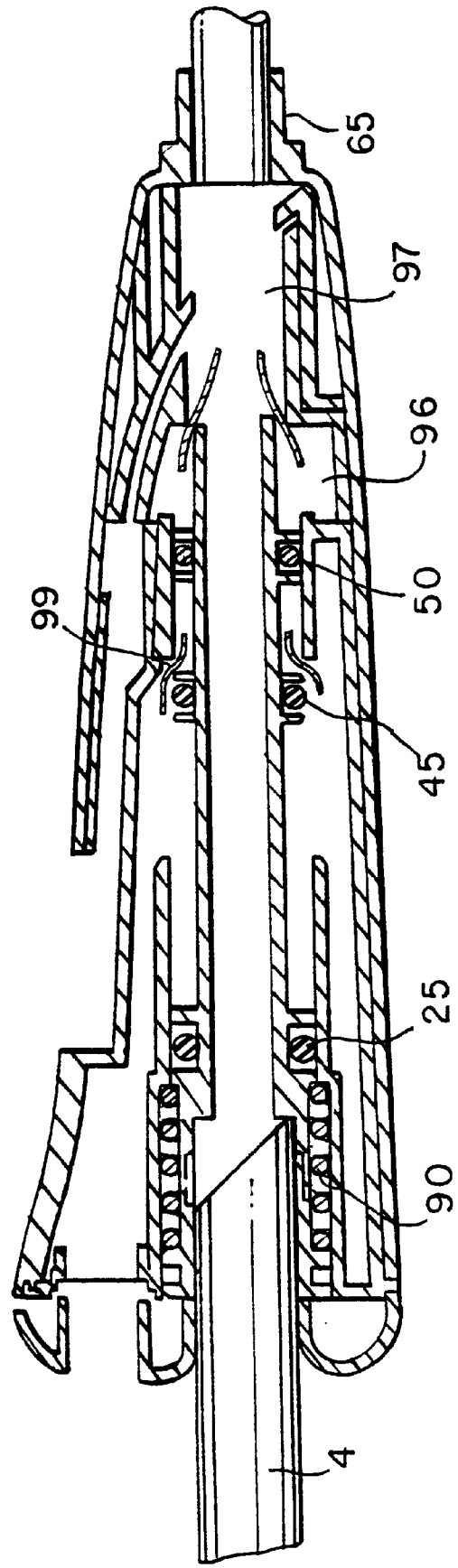
FIG. 6 shows the automatic cleaning device of FIG. 3 in a fourth position.

FIG. 3 shows the automatic cleaning device 1 according to the second embodiment of the present invention in its initial position. In this position, O-ring 50 is in contact with tab 85, and O-ring 45 is disengaged from tab 85 so that cleaning fluid from the reservoir 30 flows into the space between O-ring 45 and O-ring 50. As suction tube 4 is inserted into piston 40, springs 90 will compress, allowing piston 40 to move toward vacuum hose 2. FIG. 4 shows piston 40 in an intermediate position in which springs 90 are partially compressed and FIG. 5 shows piston 40 in a forward position with springs 90 more fully compressed. As shown in FIG. 4, since the length of tab 85 is at least equal to the distance between O-ring 45 and O-ring 50, a precise dosage of cleaning fluid is separated from the reservoir 30 and trapped between the piston 40, the O-rings 45, 50 and the tab 85 in a temporary chamber 99. Subsequently, as the piston moves into the forward position shown in FIG. 5, O-ring 50 disengages from tab 85, and the precise dosage of cleaning fluid is released into the forward chamber 96. Then, as the piston returns to the initial position, the cleaning fluid is sucked though the exit chamber 97 and into the vacuum hose 2 as shown in FIG. 6.

Figure 7:
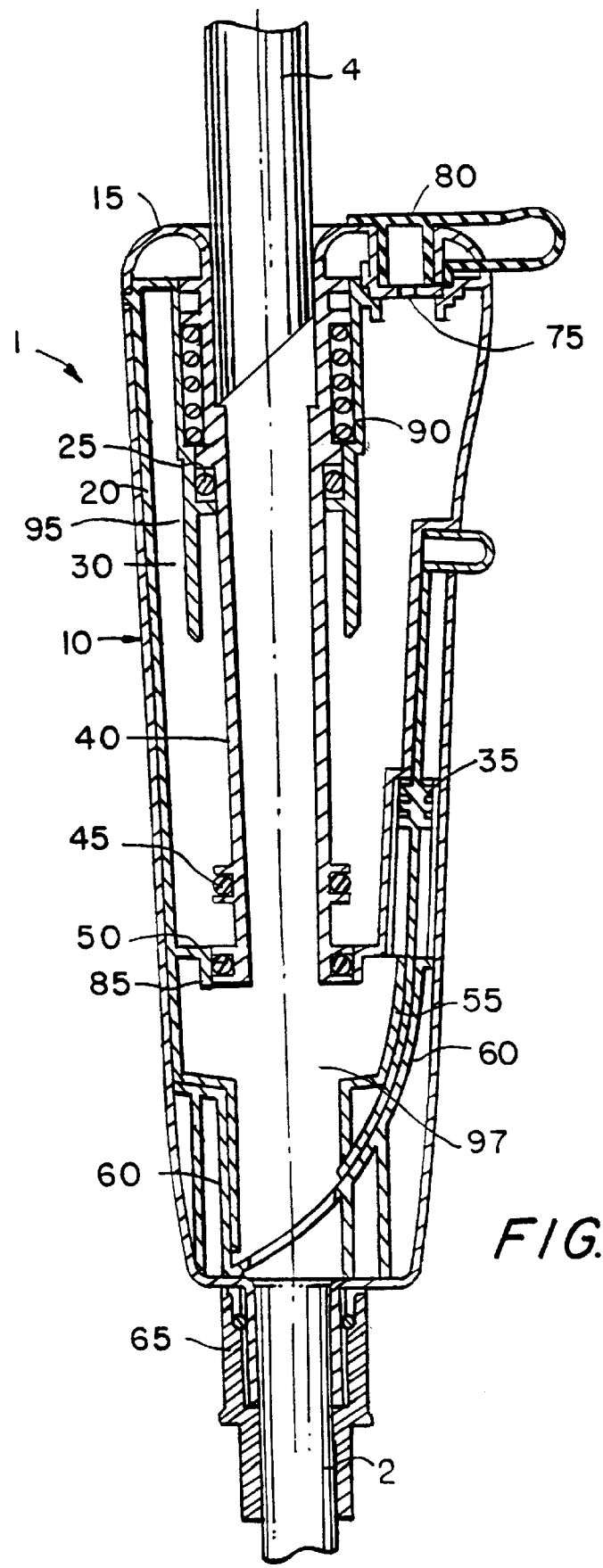
FIG. 7 shows an automatic cleaning device according to a third embodiment of the present invention.
Figure 8:
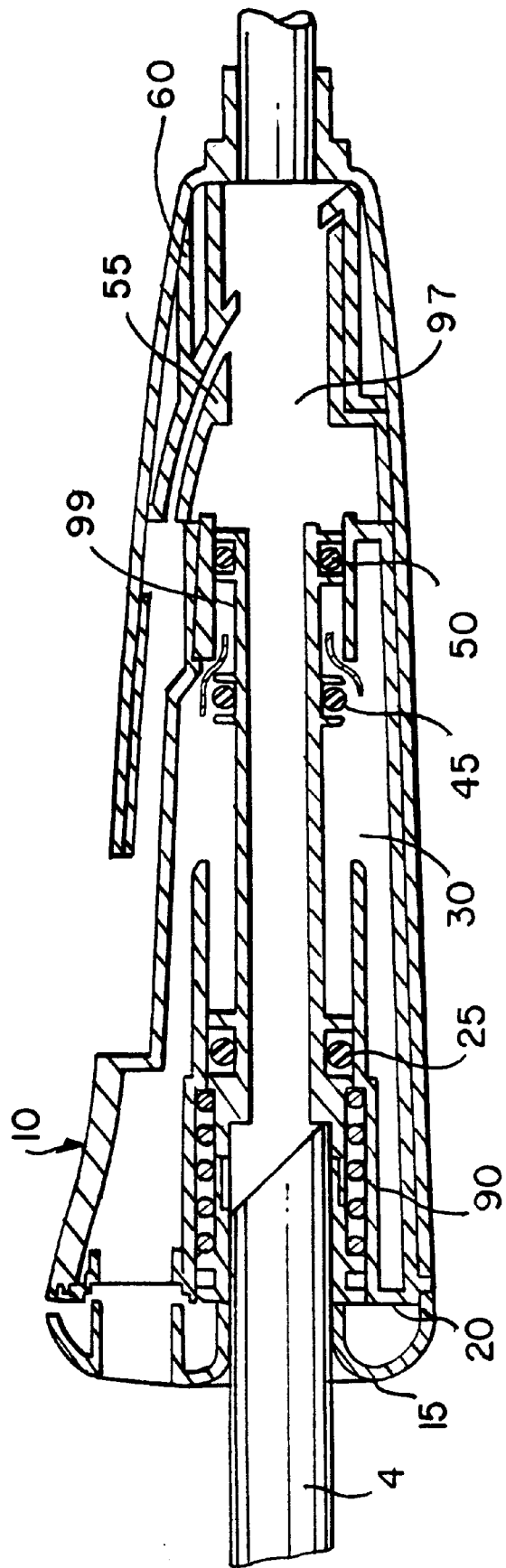
FIG. 8 shows an automatic cleaning device according to a fourth embodiment of the present invention.

In accordance with a third embodiment of the present invention, the forward chamber 96 can be eliminated, and the cleaning fluid can be released into the exit chamber 97, and sucked into the vacuum hose when the piston 40 enters the forward position. FIG. 7 shows the third embodiment in accordance with the present invention with the length of the tab 85 being less than the distance between O-rings 45, 50. With this construction, the dosage of cleaning fluid which is provided to the vacuum hose is time dependent (as described above with regard to FIG. 2). FIG. 8 shows the third embodiment in accordance with the present invention with the length of the tab 85 being greater than or equal to the distance between O-rings 45, 50. With this construction, a precise dosage of cleaning fluid is captured between O-rings 45, 50, tab 85, and piston 40, and provided to the vacuum hose (as described above with regard to FIGS. 3–6).

Figure 9A:
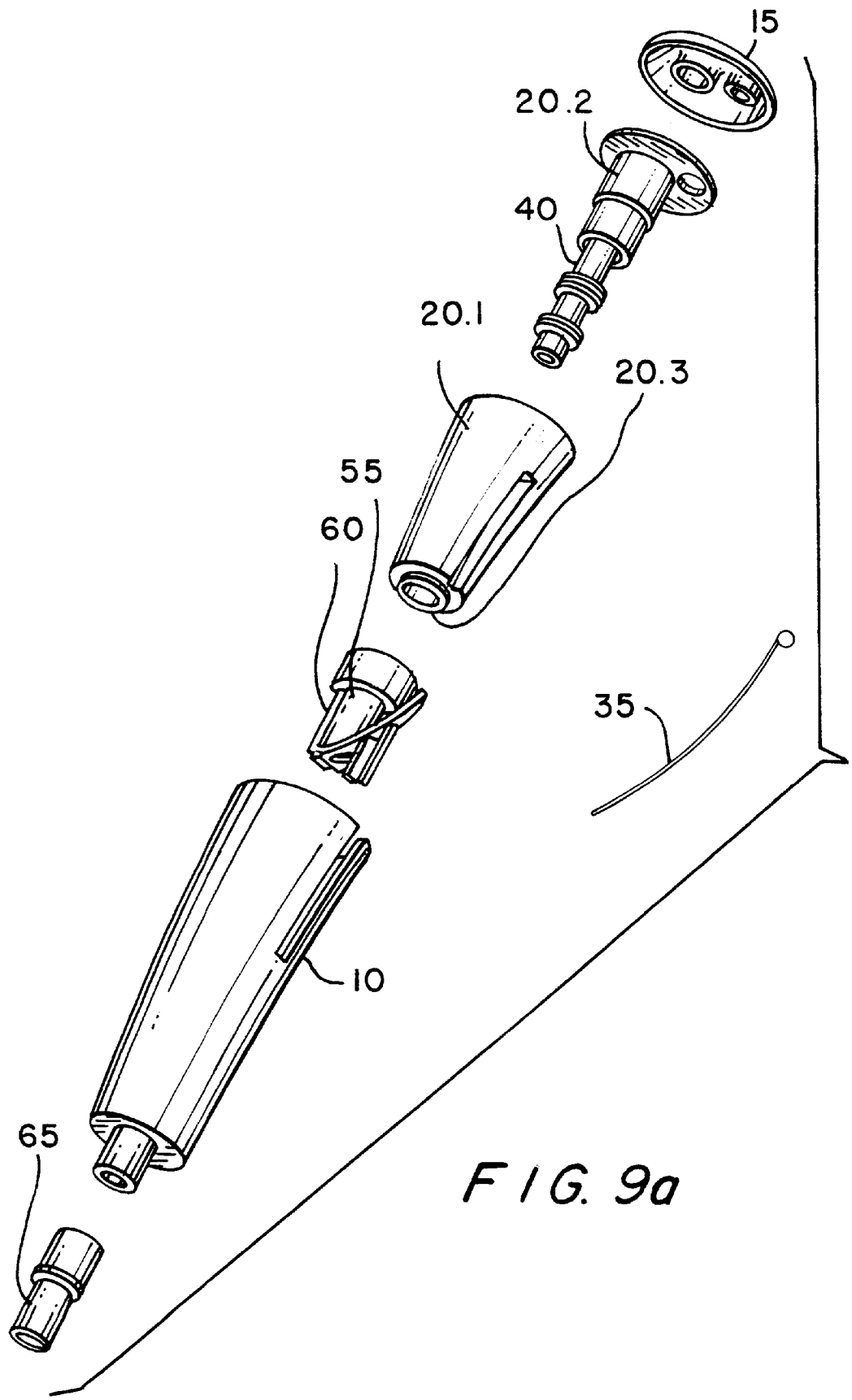
FIG. 9a shows an illustrative assembly according to an embodiment of the present invention.

FIG. 9(a) is an assembly drawing for an embodiment of the present invention. Piston 40 is telescopically mounted within reservoir top 20.2. Reservoir housing 20.1 is a hollow, substantially cylindrical member into which the piston 40 and reservoir top 20.2 are received. Tab 85 (not shown) is integral to the interior wall of the reservoir housing 20.1. In this manner, reservoir 30 is formed between piston 40, reservoir top 20.2 and reservoir housing 20.1. Reservoir housing 20.2 further includes a lip 20.3 which is received within upper reed guide 55. This assembly (reservoir top 20.2, reservoir housing 20.1, piston 40, upper and lower reed guides 55,60) is received within outer housing 10. Vacuum fitting 65 and top cap 15 are then secured to outer housing 10. Vacuum fitting 65 thus constitutes a receptacle for coupling to a vacuum hose of a vacuum system and end cap 15 constitutes another receptacle for releasably receiving a hollow member, i.e., a suction tube. Reed valve 35 is preferably mounted within the reservoir housing 20.2 and the upper and lower reed guides 55, 60 prior to insertion of the assembly into the housing. While a variety of constructions are possible in accordance with the present invention, the construction of FIG. 9a is particularly advantageous in that it is relatively simple to manufacture, and easy to disassemble for cleaning or repair.

Figure 9B:
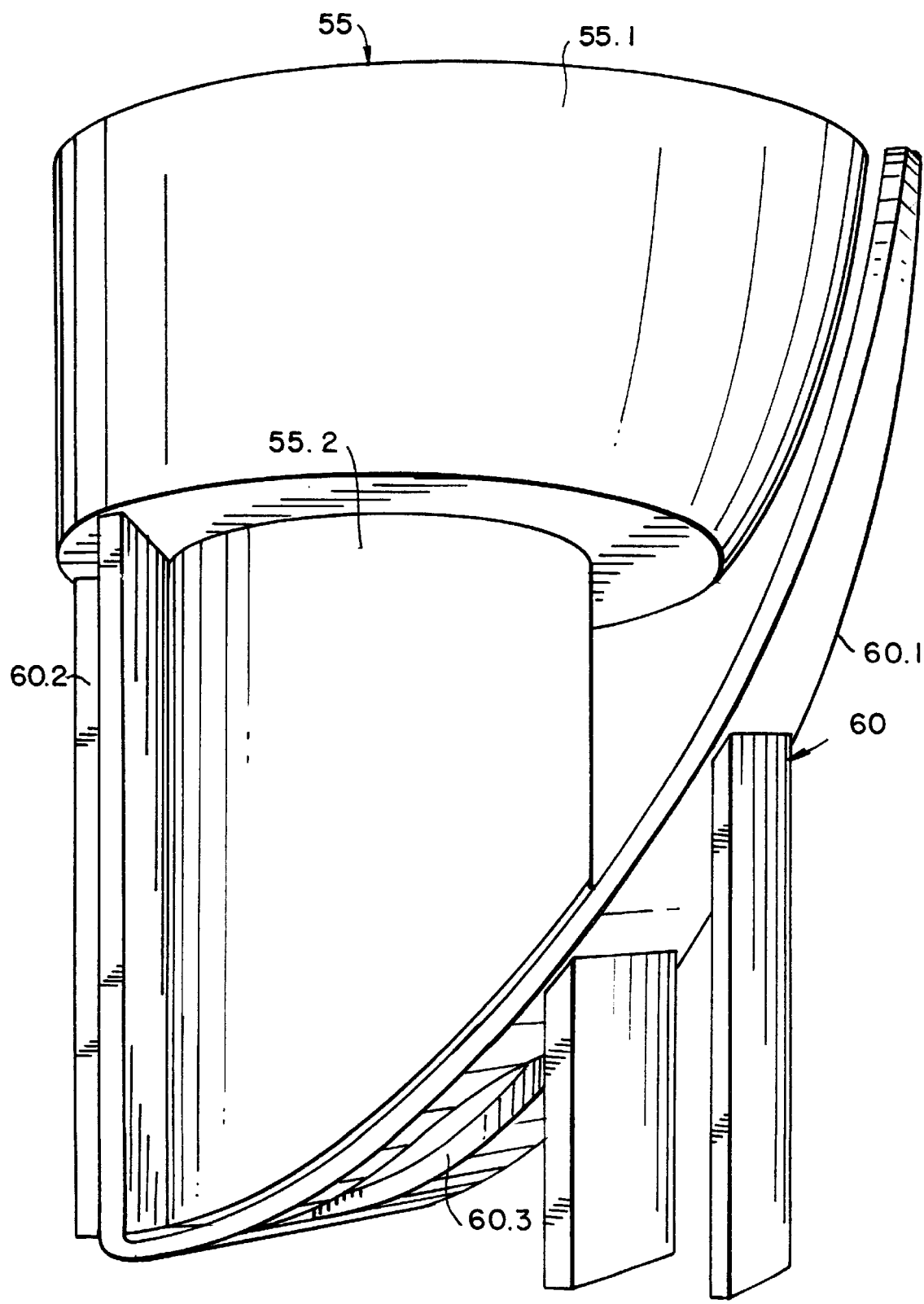
FIG. 9b shows an illustrative construction of the upper and lower reed guide according to an embodiment of the present invention.

FIG. 9b shows the upper and lower reed guide of FIG. 9a in more detail. Upper reed guide 55 is a hollow, substantially cylindrical member having a hollow cylindrical top portion 55.1 which receives the lip 20.3 of the reservoir housing 20.1. Upper reed guide 55 further includes a hollow cylindrical bottom portion 55.2, concentric with, and having a smaller diameter than, the top portion 55.1. Lower reed guide 60 includes a first portion 60.1 and a second portion 60.2. Second portion 60.2 extends along the length of bottom portion 55.2 and around a portion of the circumference thereof. First portion 60.1 is a curved member which extends from a point adjacent to cylindrical top portion 55.1 through to the second portion 60.2. An aperture 60.3 is aligned with the hollow cylindrical bottom portion 55.2. Reed valve 35 is captured in the track formed between the first portion 60.1 of the lower reed guide and the top and bottom portions 55.1, 55.2 of the upper reed guide 55. As shown, the upper and lower portions 55.1, 55.2 of the upper reed guide 55 are formed so as to provide a smooth track for the reed valve 35. Reed valve 35 is received in the track and is movable to extend across the aperture 60.3 to isolate the suction tube 4 from the vacuum hose 2. In this manner, air flow from the suction tube 4 to the vacuum hose 2 may be selectively discontinued.

What is claimed is:

1. A device for delivering a cleaning fluid, comprising
    a housing having a first receptacle at a rearward end, a second receptacle at a forward end and a fluid passageway extending between the first and second receptacles, the first receptacle for releasably receiving a hollow member, the second receptacle for coupling to a vacuum hose of a vacuum system;
    a piston slidingly mounted within the housing and biased toward the rearward end such that, upon receipt of the hollow member in the first receptacle, the piston is first moved forward in the housing against its bias and then backward to its original position to thereby effect a forward-backward movement of the piston;
    a reservoir disposed within the housing, the reservoir for housing a cleaning fluid, the reservoir operably coupled to the piston such that the forward-backward movement of the piston effects a release of the cleaning fluid to the second receptacle.

2. The device according to claim 1, further comprising biasing means arranged in the housing for biasing the piston toward the rearward end.

3. The device according to claim 2, wherein said biasing means comprise at least one spring.

4. The device according to claim 1, wherein said piston is hollow.

5. A device for delivering a cleaning fluid to a vacuum hose of a dental suction system, comprising:
    a housing having a first end and a second end, the first end for releasably receiving a hollow dental instrument, the second end for coupling to the vacuum hose;
    a reservoir disposed within the housing, the reservoir for containing a cleaning fluid;
    a hollow piston disposed within the housing and coupled to the first end of the housing such that receipt of the hollow dental instrument in the first end of the housing causes a forward-backward longitudinal movement of the hollow piston, the hollow piston providing an air-flow passage between the first end and the second end of the housing;
    a pair of longitudinally spaced apart protrusions extending outwardly from an outer surface of the hollow piston; and
    a tab arranged on the housing, the tab contacting each of the protrusions during the forward-backward movement of the hollow piston,
    the protrusions and the tab cooperating during the forward-backward movement of the hollow piston to provide for release of cleaning fluid from the reservoir into the air-flow passage between the first end and the second end of the housing such that the cleaning fluid is drawn by suction into the vacuum hose of the suction system.

6. The device according to claim 5, wherein the pair of protrusions are a pair of O-rings.

7. The device according to claim 5, wherein the reservoir has an outer wall defined by an inner wall of the housing and has an inner wall defined by the outer surface of the hollow piston, and wherein the tab extends outwardly from the inner wall of the housing.

8. The device according to claim 7, wherein a distance between the pair of protrusions is less than or equal to a longitudinal length of the tab.

9. The device according to claim 8, wherein the pair of protrusions include a pair of longitudinally spaced apart O-rings, and wherein the tab is an annular shaped member.

10. The device according to claim 5, wherein the piston is supported within the housing by a spring, the spring being compressed by the forward movement of the piston.

11. The device according to claim 5, further including a valve for selectively discontinuing a flow of air from the first end of the housing to the second end of the housing.

12. The device according to claim 11, wherein the valve is a flexible elongated member, and wherein the device further includes a valve guide disposed between the piston and the second end of the housing, the valve guide having an aperture for allowing air flow between the first and second ends of the housing, the flexible elongated member slidingly mounted within the valve guide, the flexible elongated member being movable between a first position in which the flexible elongated member covers the aperture, and a second position in which the flexible elongated member does not cover the aperture.

13. A device for delivering a cleaning fluid to a vacuum hose of a dental suction system, comprising:

a hollow dental instrument;

a vacuum hose;

a housing having a first end and a second end, the first end releasably receiving the hollow dental instrument, the second end coupled to the vacuum hose;

a reservoir disposed within the housing, the reservoir for containing a cleaning fluid;

a hollow piston disposed within the housing and coupled to the first end of the housing such that receipt of the hollow dental instrument in the first end of the housing causes a forward-backward longitudinal movement of the hollow piston, the hollow piston providing an air-flow passage between the first end and the second end of the housing;

a pair of longitudinally spaced apart protrusions extending outwardly from an outer surface of the hollow piston; and a tab arranged on the housing, the tab contacting each of the protrusions during the forward-backward movement of the hollow piston, the protrusions and the tab cooperating during the forward-backward movement of the hollow piston to provide for release of cleaning fluid from the reservoir into the air-flow passage between the first end and the second end of the housing such that the cleaning fluid is drawn by suction into the vacuum hose of the suction system.

14. The device according to claim 13, wherein the pair of protrusions are a pair of O-rings.

15. The device according to claim 13, wherein the reservoir has an outer wall defined by an inner wall of the housing and has an inner wall defined by the outer surface of the hollow piston, and wherein the tab extends outwardly from the inner wall of the housing.

16. The device according to claim 15, wherein a distance between the pair of protrusions is less than or equal to a longitudinal length of the tab.

17. The device according to claim 16, wherein the pair of protrusions include a pair of longitudinally spaced apart O-rings, and wherein the tab is an annular shaped member.

18. The device according to claim 13 wherein the piston is supported within the housing by a spring, the spring being compressed by the forward movement of the piston.

19. The device according to claim 13, further including a valve for selectively discontinuing a flow of air from the first end of the housing to the second end of the housing.

20. The device according to claim 19, wherein the valve is a flexible elongated member, and wherein the device further includes a valve guide disposed between the piston and the second end of the housing, the valve guide having an aperture for allowing air flow between the first and second ends of the housing, the flexible elongated member slidingly mounted within the valve guide, the flexible elongated member being movable between a first position in which the flexible elongated member covers the aperture, and a second position in which the flexible elongated member does not cover the aperture.

21. The device according to claim 20, wherein the valve guide includes:

an upper valve guide having a substantially cylindrical hollow top portion and a substantially cylindrical hollow bottom portion, concentric with, and having a smaller diameter than, the substantially cylindrical hollow top portion;

a lower valve guide having a first portion and a second portion, the second portion extending along a length of the hollow bottom portion and around a portion of the circumference thereof, the first portion being a curved member which extends from a point adjacent to the hollow top portion to the second portion, the second portion having an aperture which is aligned with the hollow bottom portion.

22. At The device according to claim 21, wherein the flexible elongated member is captured in a track formed between the first portion of the lower valve guide and the hollow top and hollow bottom portions of the upper valve guide.

23. The device according to claim 13, further including an auto-seal valve mounted within the housing for filling the reservoir with the cleaning fluid.

24. A device for delivering a cleaning fluid to a vacuum hose of a dental suction system, comprising:

a housing having a first end and a second end, the first end for releasably receiving a hollow dental instrument, the second end for coupling to the vacuum hose;

a reservoir disposed within the housing;

a cleaning fluid disposed within the reservoir;

a hollow piston disposed within the housing and coupled to the first end of the housing such that receipt of the hollow dental instrument in the first end of the housing causes a forward-backward longitudinal movement of the hollow piston, the hollow piston providing an air-flow passage between the first end and the second end of the housing;

a pair of longitudinally spaced apart protrusions extending outwardly from an outer surface of the hollow piston;

a tab arranged on the housing, the tab contacting each of the protrusions during the forward-backward movement of the hollow piston, the protrusions and the tab cooperating during the forward-backward movement of the hollow piston to provide for release of cleaning fluid from the reservoir into the air-flow passage between the first end and the second end of the housing such that the cleaning fluid is drawn by suction into the vacuum hose of the suction system.

* * * * *